US005874312A

United States Patent [19]
Sredni et al.

[11] Patent Number: 5,874,312
[45] Date of Patent: Feb. 23, 1999

[54] DIAGNOSIS OF ALZHEIMER DISEASE STAGE BY MONONUCLEAR CELL CYTOKINE SECRETIONS

[75] Inventors: Benjamin Sredni, Kfar Saba; Moshe Huberman, Bnei Brak; Francis Shalit, Ramat Gan, all of Israel

[73] Assignees: Bar-Ilan University, Ramat Gan; Mor Research Applications Ltd., Givet Shmuel, both of Israel

[21] Appl. No.: 782,558

[22] Filed: Jan. 10, 1997

Related U.S. Application Data

[63] Continuation of Ser. No. 257,740, Jun. 9, 1994, abandoned.
[51] Int. Cl.$^6$ .................................................. G01N 33/53
[52] U.S. Cl. ........................ 436/63; 436/811; 435/7.1; 435/7.21; 435/7.92
[58] Field of Search .................................. 435/7.1, 7.21, 435/7.92; 436/63, 811

[56] References Cited

U.S. PATENT DOCUMENTS

| | | |
|---|---|---|
| 4,728,605 | 3/1988 | Fudenberg et al. . |
| 4,886,743 | 12/1989 | Hood et al. . |
| 5,015,570 | 5/1991 | Scangos et al. . |
| 5,017,470 | 5/1991 | Aroonsakul . |
| 5,100,645 | 3/1992 | Ali-Khan et al. . |
| 5,231,001 | 7/1993 | Kaplan et al. . |

OTHER PUBLICATIONS

Berkenbosch et al, Res. Immunol, 143(6):657–63, Jul.–Aug. 1992.
McKhan etal, Neurology 34(7):939–944, Jul. 1984.
Ershler et al, Lymphokine and Cytokine Research, 12(4):225–230, 1993.
Berkow etal. eds, "The Merck Manual of Diagnosis and Therapy", pp. 1415–1417, 1987, by Merck Sharpp & Dohme Research Laboratories NJ.
Winker, JAMA, 271(13):1023–1024 Apr. 6, 1994.
AMAC Inc, AMAC Catalog of Antibodies and Immunoassays, 1992, p. 69.
Huberman et al J. Neuroimmunol, Suppl. 1, 1991, p. 17.
Glabinski et al J. Neuroimmunol., Suppl. 1, 1991 p. 17.
Gutman B. et al., J. Neuroimmunol., Suppl. 1, p. 80.
Adams & Victor (1989) "Alzheimer Disease" in *Prin. of Neur.* (McGraw Hill, NY) pp. 923–929.
Adunsky et al. (1991) "Increased cytosolic free calcium in lumphocytes of Alzheimer patients", *J. Neuroimmunol.* 33:167–172.
Bauer et al. (1992) "Participation of interleukin–6 in pathogenesis of Alzheimer's disease", *Res. in Immunol.* 143:650–657.
Bessler et al. (1989) "Lymphokine production in patients with AD", *Age and Ageing,* 18:21–25.
Boyum (1968) "Separation of Leukocytes from Human Blood" *Scan J. Clin. Lab. Invest.* 21(97)31–50.
Cserr and Knopf (1992) "Cervical lymphatics, the blood brain barrier and immunoreactivity of brain: a new view", *Immun. Today* 13:507–511.
Cunningham and DeSouza (1993) "Interleukin 1 receptors in the brain and endocrine tissues", *Immunol. Today* 14:171–176.
Esumi et al. (1991) "Serum interleukin–2 levels in patients with dementia of Alzheimer type", *Acta. Neurol. Scand.* 84:65–67.
Farrar et al. (1987) "The immune logical brain", *Immunol. Rev.* 100:361–378.
Fillit et al. (1991) "Elevated circulating tumor necrosis factor in Alzheimer's Disease", *Neurosci. Lett.* 129:318–320.
Fishman et al. (1990) "Recent advances in interleukin–3 research: A review", *Israel J. Med. Sci.* 26(7):414–419.
Flick and Gifford (1984) "Comparison of in vitro cell cytotoxic assays for tumor necrosis factor", *J. Immunol. Methods* 68:167–175.
Folstein et al. (1975) "Mini mental state: a practical method for grading cognitive state of patients for clinician", *J. Psych. Res.* 12:189–198.
Fudenberg and Singh (1988) "Alzheimer's 'syndrome': Prognosis of subsets with different etiology and preliminary effects of immunotherapy", *Drug Dev. Res.* 15:165–174.
Gautrin and Gauthier (1989) "Alzheimer's disease: environmental factors and etiologic hypotheses", *Can. J. Neurol. Sci.* 16:375–387.
Geokas et al. (1990) "The aging process", *Annals of Intern. Med.* 113:455–466.
Gillis et al. (1978) "T cell growth factor: parameters of production and quantitative microassay for activity", *J. Immunol.* 120:2027–2032.
Griffin et al. (1989) "Brain interleukin 1 and S–100 immunoreactivity are elevated in Down Syndrome/Alzheimer disease", *PNAS USA* 86:7611–7615.
Hachinski et al. (1974) "Multifarct dementia, a course of mental deterioration in the elderly", *Lancet* ii:207–208.
Hulette and Walford (1987) "Immunological aspects of AD: a review", *Alzh. Dis. Assoc. Disord.* 1:72–82.
Ikeda et al. (1991) "Interleukin–2 receptor in peripheral blood lymphocytes of AD patients", *ACTA. Psychiatr. Scand.* 84:262–265.
Kalter and Kelly (1975) "Alzheimer's disease: evaluation of immunologic indices", *NY State J. Med.* 75:1222–1225.
Licastro et al. (1990) "Zinc and thymic hormone–dependent immunity in normal ageing . . . ", *J. Neuroimmunol.* 27:201–208.

(List continued on next page.)

*Primary Examiner*—Paula K. Hutzell
*Assistant Examiner*—Patricia A. Duffy
*Attorney, Agent, or Firm*—Kohn & Associates

[57] ABSTRACT

A method of diagnosing and determining the disease stage of a degenerative disease of the central nervous system associated with the impairment of integrative brain function is disclosed. The method includes the steps of (a) measuring a cytokine production level of peripheral mononuclear cells from a peripheral blood sample and (b) determining the disease stage by comparing the level determined in step (a) with a level generated by age-matched normal controls.

1 Claim, 5 Drawing Sheets

OTHER PUBLICATIONS

Mayeux et al. (1985) "Heterogeneity in dementia of Alzheimer's type: evidence of subgroups", *Neurology* 35:453–454.

McGeer et al. (1991) "Reactions of immune system in chronic degenerative neurological diseases", *Can. J. Neur. Sci.* 18:371–379.

McKann et al. (1984) "Clinical diagnosis of Alzheimer's disease" (Report of NINCDS–ADRDA Work Group) *Neurology* 34:939–949.

McRae and Dahlstrom (1992) "Immune responses in brains of Alzheimer and Parkinson's disease patients . . . ", *Rev. Neuroscience* 3:79–97.

Merrill (1990) "Interleukin–2 effect in central nervous system", *NY Acad. Sci.* 594:188–199.

Miller et al. (1981) "Immunological studies in senile dementia of Alzheimer type: evidence for enhanced suppressor cell activity", *Ann. Neurol.* 10:506–510.

Miller (1989) "Minireview: The cell biology of aging: immun. models" *J. Gerontol.* 44:B4–B8.

Mills et al. (1985) "Increase in cytosolic free calcium concentration is an intracellular message for prod. of interleukin 2 . . . " *J. Immunol* 134:1640–1649.

Nathanson and Chun (1989) "Immuological function of blood–cerebrospinal fluid barrier", *Proc. Natl. Acad. Sci. USA* 86:1684–1688.

Ortaldo et al. (1987) "Effects of natural and recombinant IL–2 on reg. of γIFN production and natural killer activity . . . ", *J. Immunol.* 133:779–783 (Aug.).

Rogers and Rovigatti (1988) "Immunologic and tissue culture approaches to neurobiology of aging" *Neurobiol. Aging* 9:759–762.

Roth (1986) "The Association of clinical and neurological findings and bearing on class and etiology of Alzheimer's disease", *British Med. Bulletin* 42:42–50.

Skias et al. (1985) "Senile dementia of Alzheimer's type (SDAT): Red. T8+ cell–mediated supp. activity", *Neurology* 35:1635–1638 (Nov.).

Vandenabeele et al. (1991) "Is amyloidogenesis during Alzheimer's disease due to IL–1/IL–6 mediated 'acute phase response' in brain?" *Imm. Today* 12:217–219.

Weintraub et al (1982) "Daily living activities in assessment of dementia", in Alzheimer's disease: report of progress in research (Raven Press, NY) pp. 109–192.

Zatz and Goldstein (1985) "Thymosins, lumphokines and immunology of aging", *Gerontology* 31:263–277.

TNF-α PRODUCTION BY MONOCYTES OF AD PATIENTS

DIAGNOSIS OF ALZHEIMER DISEASE STAGE BY MONONUCLEAR CELL CYTOKINE SECRETIONS

This application is a continuation of application Ser. No. 08/257,740 filed on Jun. 9, 1994 now abandoned.

TECHNICAL FIELD

The present invention relates to objective methods of diagnosing the disease stage of Alzheimer's disease.

BACKGROUND OF THE INVENTION

Alzheimer's disease (AD), the onset of which occurs mainly in the later years of life, is a neurodegenerative disease causing progressive dementia.

In AD, neuropathologic examination of the brain reveals in most patients the presence of neuritic plaques, abnormal neurites, and neurofibrillary tangles containing paired helical filaments composed of cross-linked polypeptides that are especially prominent in the cerebral cortex and hippocampal formation. The mechanism of progression of the disease is unknown. The phenotype heterogeneity of the disease makes diagnosis difficult and definite diagnoses can be made only after detection of characteristic pathological changes such as neurofibrilla tangles and neuritic plaques.[1] Different etiologies have been attributed to AD, one of which has a possible immunological basis.[15]

The role of the immune system in the pathogenesis of Alzheimer's disease has been widely researched,[20,25,27] but the exact role of the immune system has not been clearly established. The fact that immune functions change with age is also well documented.[16,30,34,40] Published reports indicate a number of discrepancies concerning immunological indices associated with AD,[27] including several studies on cytokine secretion by mononuclear cells of AD patients as compared to age-matched controls,[4,29,36] and cytokine serum levels in patients with AD.[8,10] These studies suggest that immune interactions exist between the central nervous system and peripheral blood lymphocytes of AD patients. Since AD is no longer viewed today as a single unified clinical condition, but as a complex syndrome,[14] it has been postulated that the presence of different clinical subgroups may imply a differential involvement of the immune system.[23,24,35]

U.S. Pat. No. 4,728,605 to Fudenberg et al. further teaches the association of the immune system in the pathogenesis of AD, the teachings of which are incorporated herein by reference.

The presence of cytokines and their receptors in the brain, as well as the endogenous synthesis of cytokines, such as IL-1, IL-3 and IL-6, has been documented.[7,9,18,32] The physiological functions of these cytokines are virtually unknown. However, in light of the view that there is an active and highly-regulated communication between the brain and the immune system,[6,28] and as cytokines are known to function via a cascade effect, applicants postulate a link between the cytokine profile in the blood stream and that in the brain which, in turn, may have a bearing on the appearance of neurological diseases and subsequent disease progression.

There are many forms of dementia presenting with symptoms similar to AD. Many of these other conditions are treatable, such as brain tumors, thyroid and other endocrine dysfunctions, depression, infection, vitamin and mineral deficiencies, metabolic disorders, unrecognized injuries and medication side effects. AD is not treatable and so diagnosis is critical. In general, AD is diagnosed using behavioral symptoms and psychological scoring which involve subjective judgements. U.S. Pat. Nos. 4,728,605, 4,886,743, 5,015,570, 5,017,470, 5,100,645, and 5,231,001 present objective methods of diagnosing AD.

However, none of the above methods determine the stage or progression of the disease, i.e., the severity of the disease. Specifically, none of the above-listed patents or studies show any correlation between impaired cytokine production in AD and the disease stage of the patient. The determination of disease progression is still dependent on the behavioral symptoms and psychological scoring which involve subjective judgements.

Currently, the only existing FDA-approved drug for Alzheimer's is tacrine hydrochloride (Cognex™, Warner-Lambert) which is very expensive, has extensive side effects, and has been shown to be effective only in the mild stages of the disease. Therefore, an objective method of diagnosing AD at the early stages would be useful in eliciting maximal effect from this drug.

SUMMARY OF THE INVENTION AND ADVANTAGES

According to the present invention, a method of diagnosing and determining the disease stage or severity of a degenerative disease of the central nervous system (CNS) associated with the impairment of integrative brain function is disclosed. The method includes the steps of: (a) measuring a cytokine production level of peripheral mononuclear cells from a peripheral blood sample and (b) determining the disease stage by comparing the level determined in step (a) with a level generated by age-matched normal controls, thereby providing a cytokine profile for each patient. It has been determined that increases or decreases of specific cytokine production over controls reflect disease and, more particularly, the disease stage. The present invention provides an objective diagnosis and measurement of the stages of these degenerative diseases of the CNS and can provide critical information useful for treatment of the patient. The Alzheimer type of dementia is one degenerative disease of the CNS with which the present invention can be practiced.

BRIEF DESCRIPTION OF THE DRAWINGS

Other advantages of the present invention will be readily appreciated as the same becomes better understood by reference to the following detailed description when considered in connection with the accompanying drawings wherein.

DETAILED DESCRIPTION OF THE PREFERRED EMBODIMENT

Figure 1A:
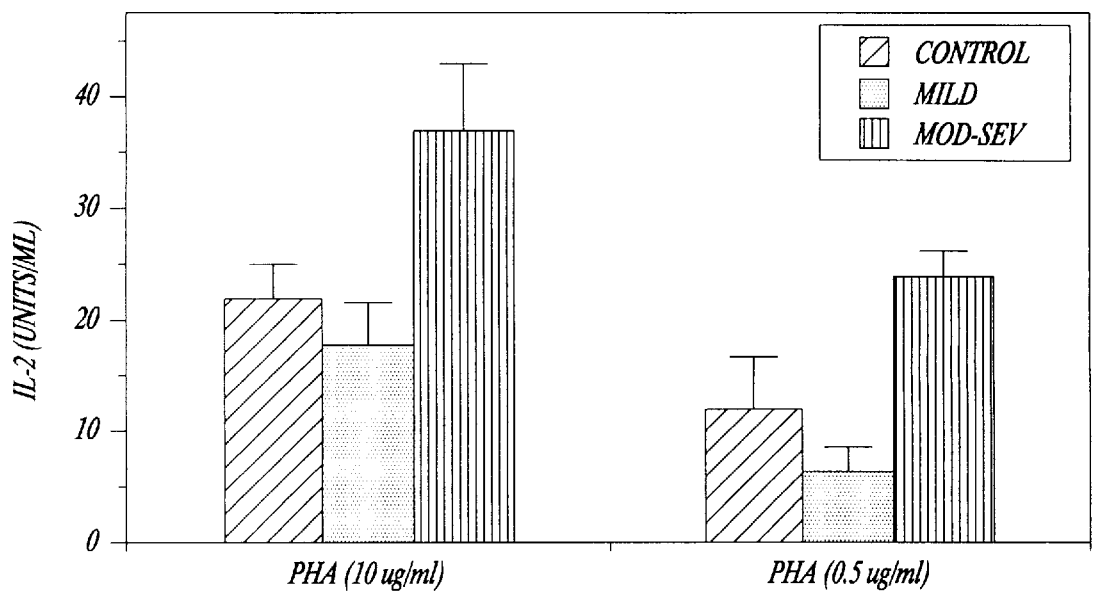
FIG. 1A is a histogram showing levels of IL-2 produced by PHA-activated mononuclear cells in AD mild and moderately-severe patients and healthy age-matched controls.

The present invention provides a method of objectively determining a patient's disease stage, or disease severity, of a degenerative disease of the central nervous system (CNS) associated with the impairment of integrative brain function. The Alzheimer type of dementia is one degenerative disease of the CNS with which the present invention can be practiced.

The patient's blood is drawn and mononuclear cells (MNC) are isolated and, where appropriate, monocytes were separated by plating $5 \times 10^6$ MNC per well in 24-well culture plates for 1 hour at 37° C. and 7.5% $CO_2$, followed by removal of nonadherent cells.

The cells are then cultured and the media analyzed for the presence of cytokines released by the cells. Similarly, the levels in healthy age-matched controls (OC) are also determined.

The assays can be either bioassays, ELISAs or RIAs. Various cytokines can be assayed and the culture conditions varied to allow production of the cytokine of interest. For example, mitogens, such as PHA and LPS, can be added to the media during the culture period to cause the production of IL-2 and IFN-α or TNF-γ and IL-1β, respectively, as described hereinbelow.

In the final step of the present invention, the cytokine levels of the AD patient are compared to those of the OC control, providing a cytokine profile of each patient tested. It has been determined that increases of IL-2, TNF-α, IFN-γ, and IL-6 production over controls indicates a moderately-severe disease stage, while a decrease of IL-3-LA levels and an increase of IL-6 levels from control levels indicates a mild disease stage. The present invention provides an objective measurement of the stages of these degenerative diseases of the CNS.

In the present invention, cytokine secretion in AD patients in the mild and moderately severe stage of the disease was evaluated. This is the first comparative method utilizing cytokine secretion by MNC of AD patients correlated with the patients' clinical condition. The present invention focuses on immune changes associated with AD, independent of changes in the normal aging population.

Several studies on cytokine production of AD patients have been reported.[4,8,10,29,36] The results obtained when testing cytokine secretion in AD patients before clinical subdivision were in line with those of Miller et al.[30] and Bessler et al.[4] who report no differences in IFN-γ, IL-1β, and Il-2 production levels by mononuclear cells between AD patients and their age-matched controls.

However, in the present invention, when the patients were divided into the mild and moderately severe groups, a different cytokine profile emerged. A significant decrease in IL-3-LA and increase in IL-6 production levels in the mild AD group as compared to OC was observed. In the moderately-severe AD group, there was a significant increase in IL-2, IFN-γ, IL-6, and TNF-α production as compared to OC and IL-3-LA levels were higher (though not significantly) than those of the mild group, approaching control levels.

Increased cytosolic-free calcium levels in lymphocytes of AD have been reported.[2] This finding supports the observation herein of increased IL-2 secretion, for calcium is pivotal as a transmembrane messenger in the activation signal for T lymphocytes and in eliciting transcription of the IL-2 gene.[31]

The relationship between increased production of IL-2 and IFN-γ can be understood in light of the fact that the lymphokine IL-2 is one of the interferon inducers.[33] These findings may imply the presence of augmented TH1 clones (secretors of IL-2 and IFN-γ) in the moderately severe stage of the disease. TH1 subsets have been shown to provide B cell help for IgM, IgG, and IgA synthesis known to be elevated in the more advanced stages of AD disease.[22]

To conclude, the results show a correlation between production levels of IL-2, IFN-γ, TNF-α, IL-3-LA, and IL-6 by mononuclear cells (MNC) of Alzheimer patients and the clinical condition of these patients. These results indicate that immunologically defined substages of AD may serve as diagnostic markers in the progression of the disease.

Immunological changes occurring in patients with AD have not been sufficiently clarified or defined so far. These results show for the first time that changes occurring in patients with mild AD are not expressed in patients with moderately-severe AD (i.e. decrease in IL-3-LA). Furthermore, the cytokine profile observed in moderately-severe patients was not seen in mild AD patients.

A kit providing the appropriate reagents to measure IL-2, IFN-γ, TNF-α, IL-3-LA, and IL-6, as well as the appropriate age-matched control samples, can be made with the present invention. By providing the age-matched controls, standardization of the assay and interpretation of results can be obtained.

The above discussion provides a factual basis for the use of cytokines as an objective determination of the disease stage of cognitive disorders such as AD. The methods used with and the utility of the present invention can be shown by the following examples.

EXAMPLES

Subjects and Methods

Subjects: Thirty-six patients, 22 females and 14 males, with senile dementia of the Alzheimer type (mean age 76.6±3 years), and 30 age and sex-matched controls (mean age 74±2.2 years) were studied. All the patients were living in their homes and attended the same day-care unit. Age-matched elderly controls (OC) consisted of healthy elderly subjects without cognitive impairment according to the Record on Independent Living (RIL) criteria.[39] An additional control group of 10 patients diagnosed as severe multiple infarct dementia (MID) according to the Hachinski et al.[19] criteria was included in several of the experiments. All participants were free of any medication or diseases known to affect lymphocyte function and two blood samples were drawn from each participant within a two-week interval to exclude possibility of intercurrent infection which may affect the immune system.

Clinical diagnosis and intellectual performance tests. Diagnosis of AD patients was based on NINCDS-ADRDA criteria.[26] Biochemical and metabolic parameters such as total blood count, blood chemistry, B12, Folic acid and VDRL and thyroid function tests were evaluated. Patients were also monitored by electroencephalogram (EEG) and computed tomography (CT) brain scanning.

Severity of dementia was assessed in AD patients using the RIL criteria. Patients were divided into two subgroups: mild dementia (score 17–32) and moderately-severe dementia (score 33–64). The mild dementia group consisted of 17 patients, 10 females and 7 males (mean age 75.8±3.1 years); and the moderately-severe dementia group consisted of 19 patients, 12 females and 7 males (mean age 77.4±2.9 years). The minimum Mental State (MMS) test[13] was performed to confirm the level of impairment of each subgroup; mild AD patients group score (16.85±3.86) was significantly higher than those of the moderately-severe patients (6.2±1.39).

Cell isolation. Human mononuclear cells (MNC) were separated from fresh heparinized blood of healthy donors and AD patients by Ficoll-Hypaque density gradient centrifugation (Pharmacia, Fine Chemicals, Uppsala, Sweden) as described by Boyum.[5]

IL-2 production and quantification. Human MNC, $1.5 \times 10^6$/ml, were suspended in enriched RPMI-1640 (Gibco) culture medium supplemented with 10% Fetal Calf Serum (FCS), 2 mM L-glutamine, 10 mM nonessential amino acids, 3mM sodium pyruvate, $5 \times 10^{-5}$ 2-mercaptoethanol (2-ME), and incubated at 37° C. in the presence of 10 or 0.5 μg/ml phytohemagglutanin (PHA-M; Gibco) for 48 hours. In addition, kinetic studies wherein cells were incubated for 24, 48, and 72 hours were carried out on five samples from each group. Supernatants were collected and assayed for IL-2 activity.[17] The ability of the supernatant fraction to support the growth of the IL-2-dependent CTLL clone was used to assay IL-2 production (bioassay). CTLL cells ($10^4$ per well) were seeded in triplicate in culture medium, with or without dilutions of the supernatant fractions. After 48 hours, [$^3$H]thymidine uptake was determined in a liquid scintillation counter. One unit of IL-2 activity was defined as the reciprocal log 2 dilution required to give 50% of the maximal proliferation of $10^4$ IL-2 dependent murine CTLL after 48 hours of culture. A commercially available ELISA test (Advanced Magnetics, USA) was also used for quantification of human IL-2 in the supernatant fraction.

IL-3-LA production and assay. Human IL-3-LA was tested in a bioassay as described by Fishman et al.[11] This human growth factor is spontaneously produced by monocytes and lymphocytes. Human MNC cells, $3 \times 10^6$/ml, were suspended in RPMI-1640 supplemented with 10% FCS and incubated for 48 hours at 37° C. Supernatants were collected and IL-3-LA activity was assayed by its ability to stimulate the proliferation of the IL-3 responsive cell line 32D-c123. Briefly, 0.1 ml of 32D-c123 cells ($10^4$ per well) were seeded in triplicate in culture medium with or without dilution of the supernatant fraction. Cultures were incubated for 24 hours at 37° C. Each well was pulsed with 1 μCi [$^3$H]thymidine for the final six hours of culture. Thymidine uptake was determined in a liquid scintillation counter. One unit of Il-3-LA activity was defined as the reciprocal log 2 dilution required to give 50% of the maximum proliferation of $10^4$ 32D-c123 cells after 48 hours of culture. The standard was recombinant murine IL-3 (Genzyme, Boston, Mass.).

TNF-α secretion and bioassay. Human monocyte cultures were obtained by adhering $5 \times 10^6$ MNC to 24 well tissue culture plates for 1 hour at 37° C., followed by removal of nonadherent cells. The resulting monolayers were reconstituted with enriched RPMI medium and cultured with LPS (Sigma, 10 μg/ml) for 6 hours. The TNF-a content in supernatants thus obtained was evaluated using a commercially available ELISA kit (Advanced Magnetics, USA). Alternatively, TNF-α could be measured by a cell cytotoxicity assay.[12]

IL-6 secretion and quantification. Secretion of IL-6 was obtained under culture conditions previously described for production of IL-2. The IL-6 content in supernatant fractions was measured using a commercially available ELISA kit from Advanced Magnetics, USA.

IFN-γ secretion and bioassay. IFN-γ levels were tested in supernatants prepared by the same method as that for human IL-2. Supernatants were assayed by a commercially available ELISA kit (T-Cell Sciences, Cambridge, Mass.).

IL-1β secretion and quantification. For the production of IL-1β, $5 \times 10^6$/ml MNC were suspended in enriched RPMI and incubated for one hour at 37° C. Nonadherent cells were thereafter washed out of the tissue culture plate and the remaining adherent cells were cultured in enriched RPMI-1640 supplemented with 10 μg/ml lipopolysaccharide (LPS, Sigma) for six hours. Supernatants were assessed by a commercially available ELISA kit (Cistrom Biotechnology, Pine Brook N.J.).

Statistical Analysis. Mean values were compared by the (nonparametric) Wilcoxon test.

Results

Cytokine production levels were measured in age-matched elderly controls and AD patients subdivided into mild and moderately-severe groups. Table 1 shows patient characteristics compared to healthy controls.

TABLE 1

Study Group Characteristics

|  | AD*-mild | AD* moderately-severe | control |
|---|---|---|---|
| Number of patients | 17 | 19 | 30 |
| Gender (M/F) | 7/10 | 7/12 | 12/18 |
| Age (years)b | 75.8 ± 3.1 | 77.4 ± 2.9 | 74 ± 2.2 |
| Mini-mental score[b] | 16.85.5 ± 3.85 | 6.2 ± 1.39 | 29.5 ± 0.78 |

*AD, Alzheimer's disease
[b]- values are mean ± SD

Example 1

Levels of IL-2 Production by PHA-Activated Mononuclear Cells

Figure 1B:
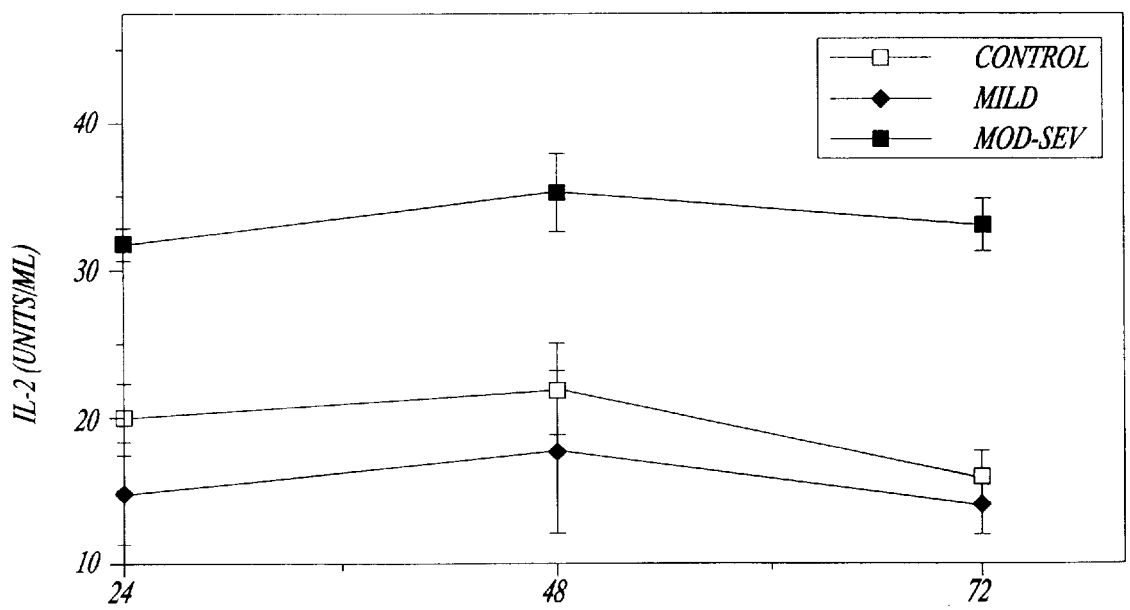
FIG. 1B is a graph showing levels of IL-2 produced by PHA-activated mononuclear cells over time in AD mild and moderately-severe patients and healthy age-matched controls.

Levels of IL-2 production by PHA activated (10 μg/ml) MNC after 48 hours of incubation are shown in FIG. 1A. There was a significant increase in IL-2 levels secreted by MNC of moderately-severe AD patients as compared to the other two groups (37.1±6 U/ml vs. 17.49±4.2 U/ml (mild), and 19±4.1 U/ml (OC) ($p<0.01$; $p<0.01$). No significant difference was observed in IL-2 secretion between mild AD patients and OC. Similar results were obtained when MNC were incubated with a sub-optimal dose of PHA (0.5 μg/ml): moderately severe levels (24±2.3 U/ml) vs. mild levels (6.1±2.9 U/ml) and control levels (13.2±4.7 U/ml), $p<0.02$. Kinetic studies were subsequently performed on five samples from each experimental group. As can be seen in FIG. 1B, IL-2 levels of production in the moderately-severe group were significantly higher at all time points ($p<0.01$) as compared to both mild and OC groups. IL-2 production levels in the mild group were slightly lower though non-significant compared to the control group.

Figure 1C:
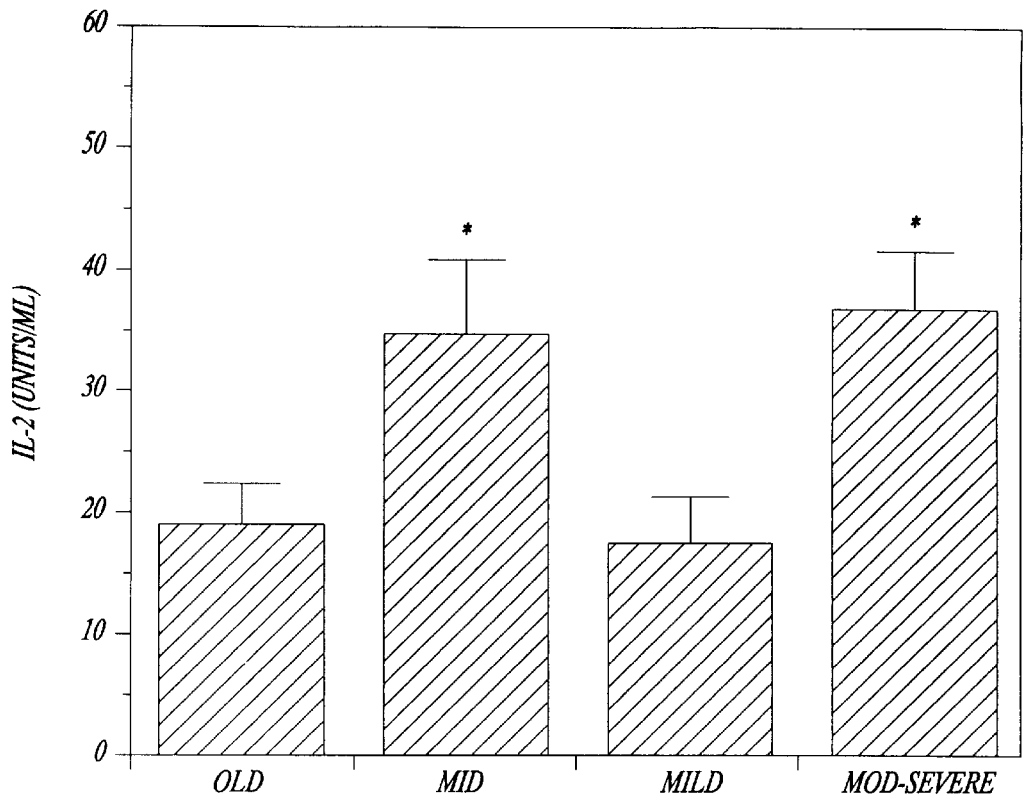
FIG. 1C is a histogram showing levels of IL-2 produced by PHA-activated mononuclear cells and measured by a bioassay in AD mild and moderately-severe patients, MID patients and healthy age-matched controls.

In a second experiment, MID patients (average age 76.6±49 years) were included. As can be seen in FIG. 1C, levels of IL-2 secretion in MID patients, as measured by bioassay, are significantly higher than that of healthy elderly control subjects and mild AD patients (p>0.01). The MID results do not differ significantly from moderately-severe patients. These results suggest that elevated IL-2 levels may reflect the degree of severity of dementia rather than specificity of dementia.

Figure 1D:
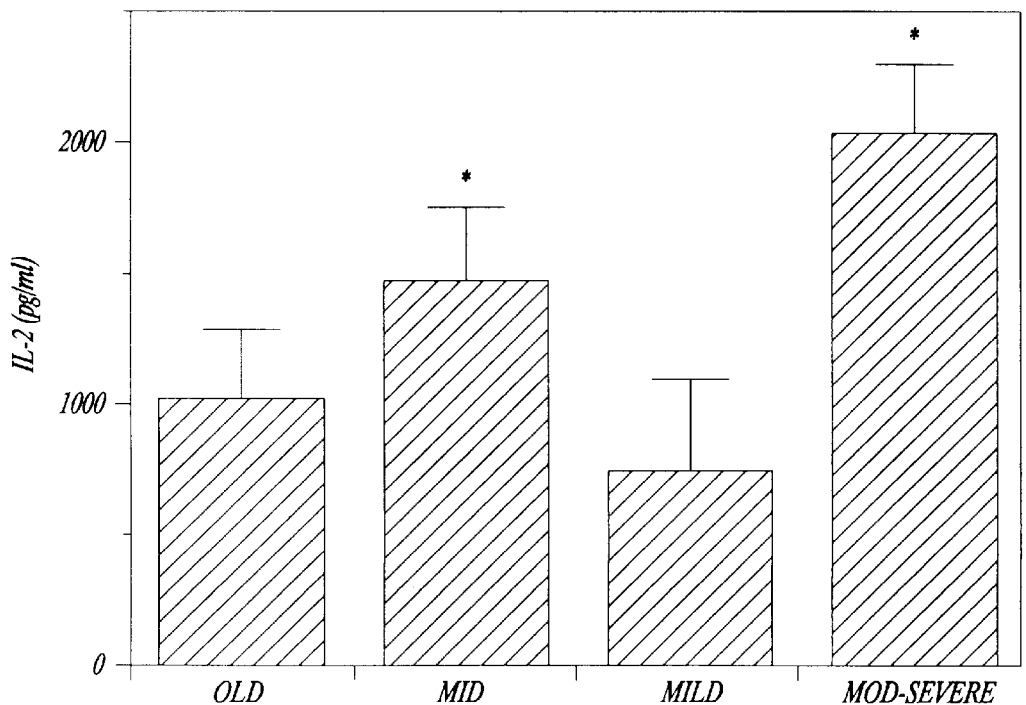
FIG. 1D is a histogram showing levels of IL-2 produced by PHA-activated mononuclear cells and measured by an ELISA in AD mild and moderately-severe patients, MID patients and healthy age-matched controls.

In a third experiment, IL-2 secretion as measured by ELISA was determined in healthy elderly control subjects, MID patients, and AD mild and moderately-severe patients. As seen in FIG. 1D, the results parallel those seen with the bioassay. IL-2 secretion is a marker of moderately-severe dementia patents.

Example 2

Levels of IFN-$\gamma$ Production by T-Helper Cells

Figure 2:
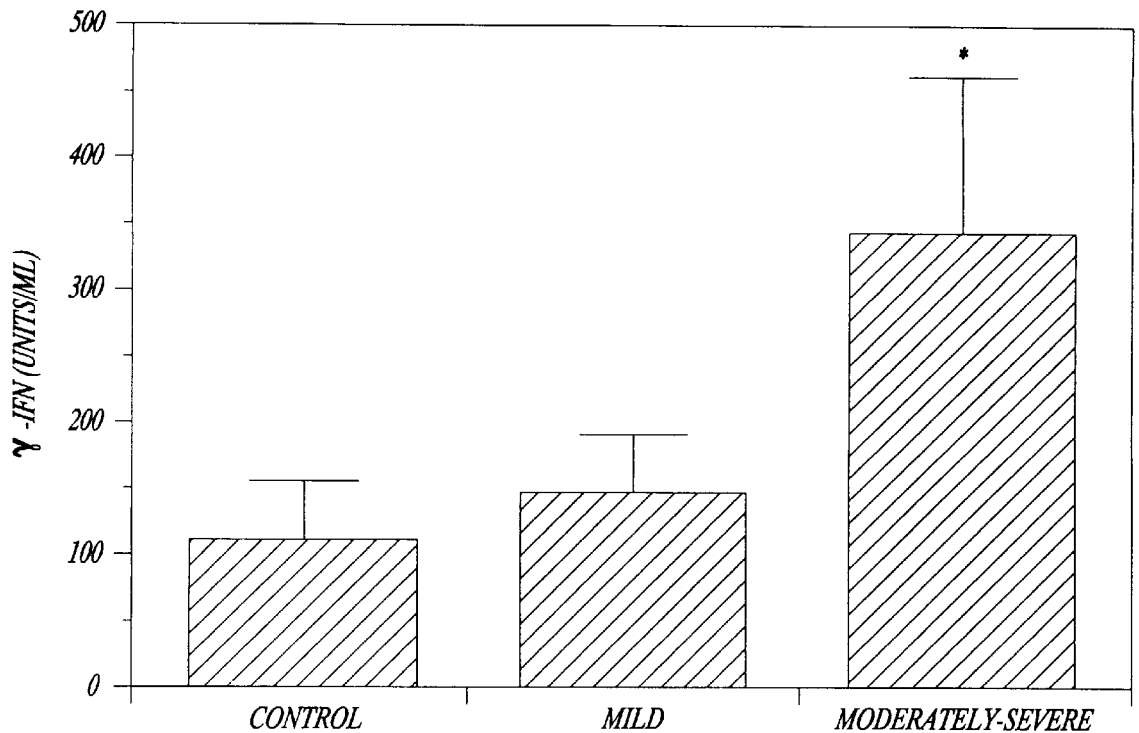
FIG. 2 is a histogram showing levels of IFN-γ production by T-helper cells in groups as listed in FIG. 1A.

The production levels of IFN-$\gamma$ were assayed. IFN-$\gamma$ is also secreted by T-helper cells and augmented by the presence of IL-2. Results similar to those of IL-2 were obtained for IFN-$\gamma$ levels when tested in supernatants from PHA optimally-stimulated MNC incubated for 48 hours. As may be seen in FIG. 2, the levels of IFN-$\gamma$ secretion of moderately-severe AD patients were significantly higher when compared to OC (342±119 U/ml patients vs. 11.75±37.8 U/ml, p<0.05), and higher, though not significantly, than in the mild group. No differences were observed between mild AD patients and OC.

Example 3

Levels of IL-3-LA Production by Mononuclear Cells

Figure 3:
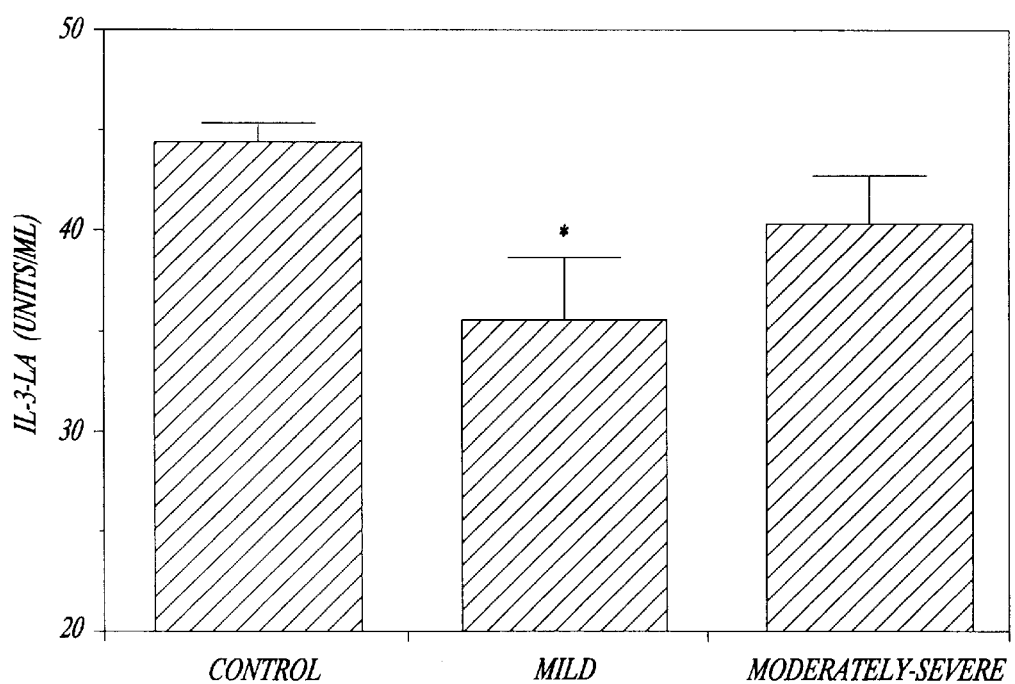
FIG. 3 is a histogram showing levels of IL-3-LA production by mononuclear cells in groups as listed in FIG. 1A.

The cytokine and IL-3-LA is secreted both by macrophages and lymphocytes. IL-3-LA has been found to be endogenously synthesized in the brain and, therefore, it was of interest to test levels of production by MNC in varying stages of AD. FIG. 3 summarizes the levels of spontaneous IL-3-LA secretion in supernatants from MNC cells incubated for 48 hours. As may be seen, a significant decrease in IL-3-LA levels was observed in mild AD patients compared to OC (44.4±0.94 U/ml vs. 35.43±3.25 U/ml, p=p.01). Results indicated a small, though not significant, increase in the moderately-severe groups as compared to the mild group, suggesting a return to control levels.

Example 4

Levels of TNF-$\alpha$ Production by LPS-Activated Monocytes

Figure 4:
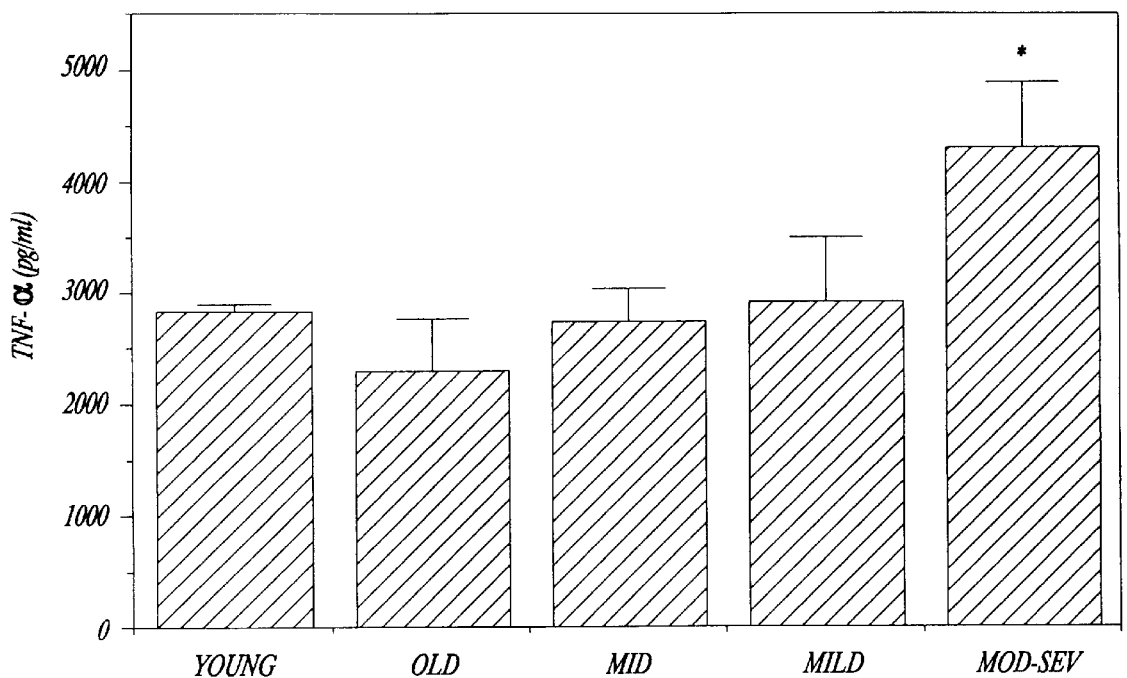
FIG. 4 is a histogram showing levels of TNF-α production in LPS-activated monocytes cells, measured by ELISA, in AD mild and moderately-severe patients, MID patients, healthy age-matched controls and healthy young subjects.

TNF-$\alpha$ levels were measured in AD mild and moderately-severe patients, MID patients, healthy age-matched controls and healthy young subjects utilizing an ELISA kit. As can be seen in FIG. 4, a significant increase (p<0.01) in TNF-$\alpha$ production was found in the moderately-severe group as compared to other experimental groups.

Example 5

Levels of IL-1$\beta$ Production by Activated Macrophages

Figure 5A:
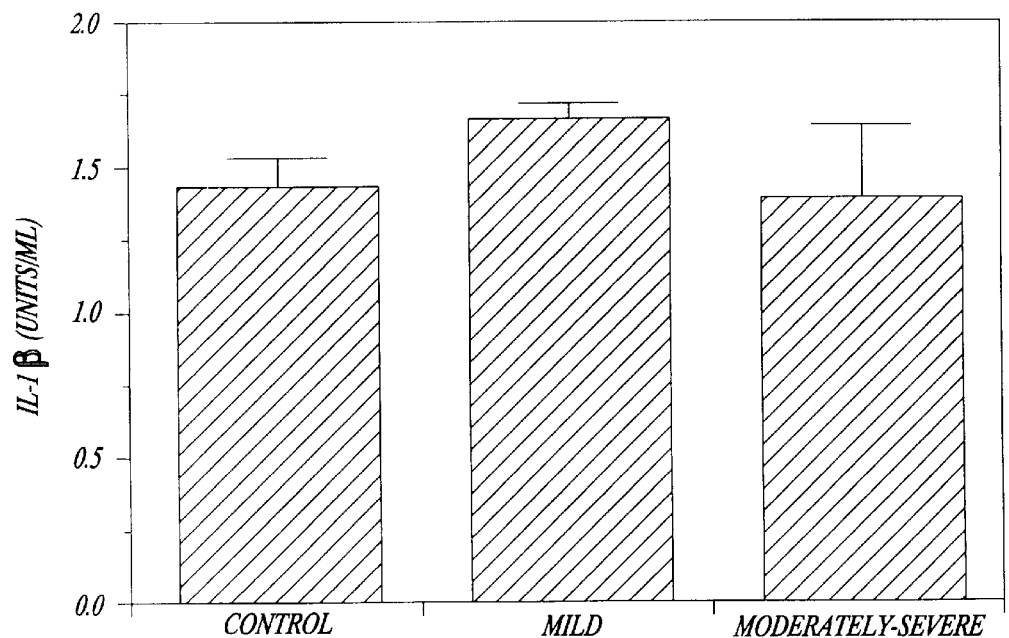
FIG. 5A is a histogram showing levels of IL-1β production by activated monocytes in groups as listed in FIG. 1A.

Levels of IL-1$\beta$ secretion were determined. IL-1$\beta$ is a monokine secreted by activated macrophages and found to be secreted in the central nervous system. No differences in IL-1$\beta$ production levels were observed when age-matched healthy controls were compared to AD patients (FIG. 5A).

Figure 5B:
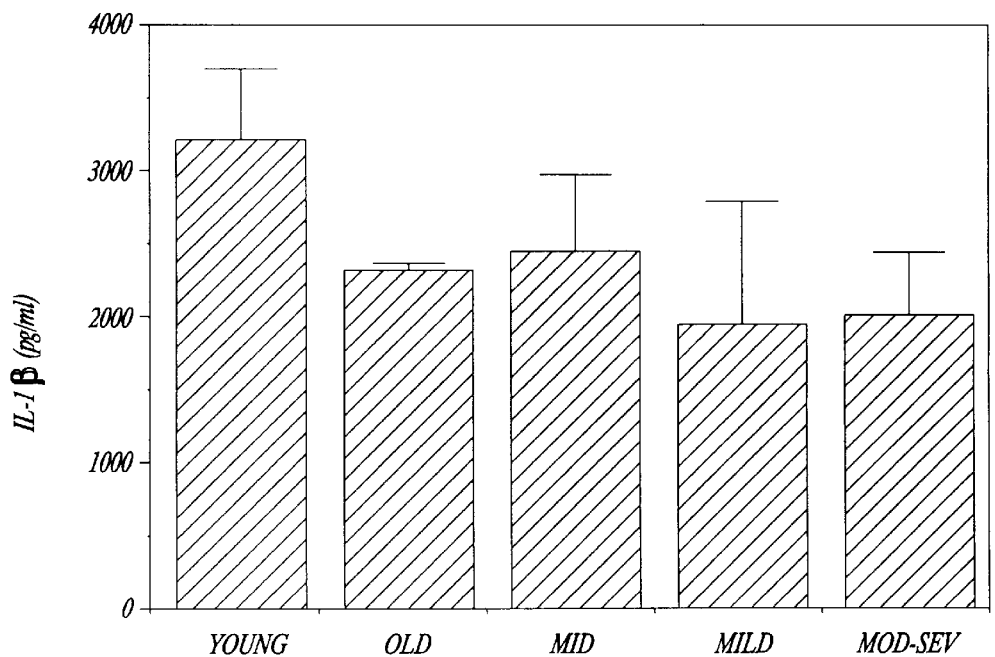
FIG. 5B is a histogram showing levels of IL-15 production by activated macrocytes in AD mild and moderately-severe patients, MID patients, healthy age-matched controls and healthy young subjects.

In a second experiment, a second control group consisting of ten MID patients (mean age 76.6±4.9) was also evaluated, as well as healthy young subjects (mean age 46.8±4.9 years). As seen in FIG. 5B, no significant differences were found between the age-matched controls, MID patients, and the AD patients.

Example 6

Levels of IL-6 Production by PHA-Activated Mononuclear Cells.

Recent studies[3,19,37] have proposed the concept of an interleukin-6 (IL-6) mediated-cerebral acute phase response as an element of Alzheimer's disease (AD) pathophysiology. This concept stems from the fact that amyloid in the senile plaques is tightly associated with acute-phase proteins which are known to be mediated by interleukin-6. Increase serum levels of acute-phase proteins have been reported in AD;[21] however, serum levels of IL-6 were not found to be elevated in AD.

Figure 6:
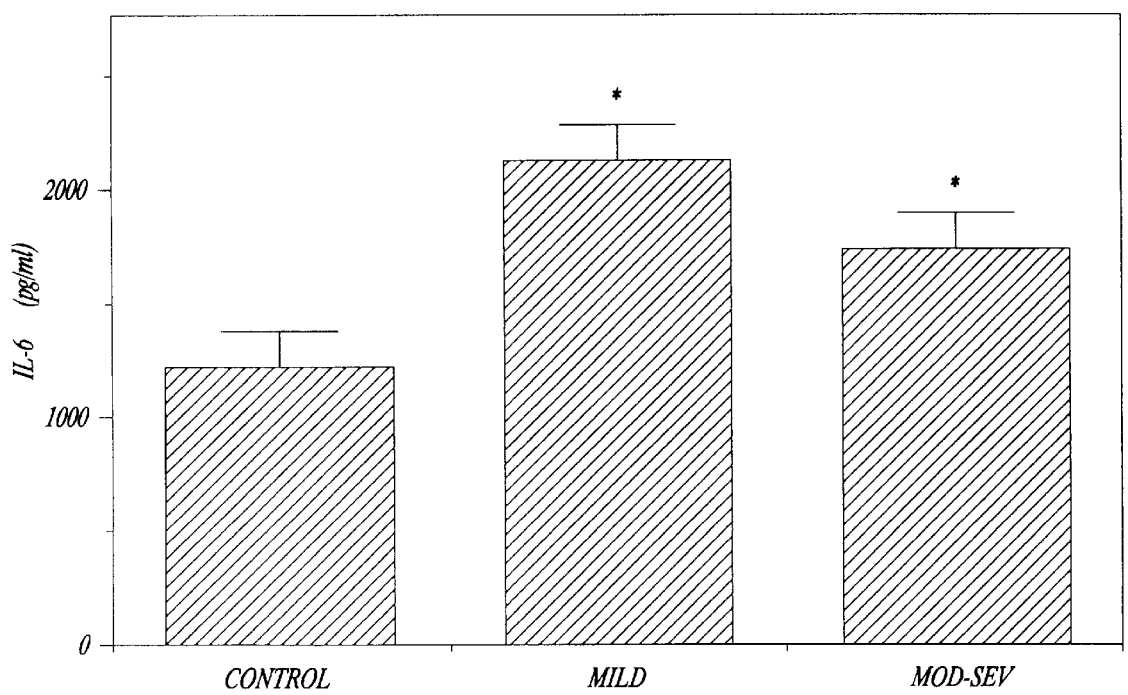
FIG. 6 is a histogram showing levels of IL-6 production by PHA-activated mononuclear cells in groups as listed in FIG. 1A.

As can be seen in FIG. 6, a significant increase in IL-6 production was seen both in the mild and moderately severe groups as compared to elderly controls (mild: 2136±311 pg/ml; moderately severe: 1750±144 pg/ml vs. OC: 1209±166 pg/ml, p<0.01). These results indicated that IL-6 secretion by mononuclear cells can serve as a marker for AD; and, in particular, indicate different stages of the disease.

In addition to the elderly age and sex-matched controls, a second control group consisting of severely demented patients, i.e., multiple infarct dementia patients (MID) were included. In these studies, IL-6 levels in MID patients (1393±174 pg/ml) were not significantly different from that of elderly controls (1209±166 pg/ml) and were significantly increased compared to the mild (2136±311 pg/ml) and moderately severe (1750±144 pg/ml) AD groups (p<0.02).

In summary, cytokine secretion by human mononuclear cells (MNC) was investigated in age-matched controls and in patients with Alzheimer's disease (AD). AD patients were divided into two study groups: "mild" and "moderately-severe" based on psychosocial testing.

A significant increase in interleukin-2 (IL-2), gamma interferon (IFN-$\gamma$), tumor necrosis factor-$\alpha$ (TNF-$\alpha$), and interleukin-6 (IL-6) secretion was found in AD patients in the moderately-severe stage of the disease; whereas, in the mild stage of the disease, there was a significant decrease in interleukin-3 (IL-3-LA) like activity and increase in IL-6 activity. No significant differences were found in the level of production of interleukin-1$\beta$ (IL-1$\beta$).

These results demonstrate the existence of defective immune functions in AD patients which are correlated with the disease stage of these patients and can be used to objectively diagnose disease and determine the disease stage. The determination of the disease stage can be used to determine which treatment would be most effective.

The invention has been described in an illustrative manner, and it is to be understood that the terminology which has been used is intended to be in the nature of words of description rather than of limitation.

Obviously, many modifications and variations of the present invention are possible in light of the above teachings. It is, therefore, to be understood that within the scope of the appended claims, the invention may be practiced otherwise than as specifically described.

REFERENCES

1. Adams and Victor (1989) "Alzheimer Disease", in *Prin. of Neur.*, McGraw Hill Inf. Services, NY, pp. 923–929.
2. Adunsky et al. (1991) "Increased cytosolic free calcium in lymphocytes of Alzheimer patients", *J. Neuroimmunol.* 33:167–172.

3. Bauer et al. (1992) "The participation of interleukin-6 in the pathogenesis of Alzheimer's disease", *Res. in Immunol.* 143:650–657.
4. Bessler et al. (1989) "Lymphokine production in patients with Alzheimer disease", *Age and Ageing*, 18:21–25.
5. Boyum (1968) "Separation of leukocytes from blood and bone marrow", *Scand. J. Clin. Lab. Invest.* Vol. 21 (suppl. 97), 31–50.
6. Cserr and Knopf (1992) "Cervical lymphatics, the blood brain barrier and immunoreactivty of the brain: a new view", *Immunol. Today* 13:507–511.
7. Cunningham and DeSouza (1993) "Interleukin 1 receptors in the brain and endocrine tissues", *Immunol. Today* 14:171–176.
8. Esumi et al. (1991) "Serum interleukin-2 levels in patients with dementia of Alzheimer type", *Acta. Neurol. Scand.* 84:65–67.
9. Farrar et al. (1987) "The immune logical brain", *Immunol. Rev.* 100:361–378
10. Fillit et al. (1991) "Elevated circulating tumor necrosis factor in Alzheimer's disease", *Neurosci. Lett.* 129:318–320.
11. Fishman et al. (1990) "Recent advances in interluekin-3 research: A review", *Israel J. Med. Sci.* 26:414–419.
12. Flick and Gifford (1984) "Comparison of in vitro cell cytotoxic assays for tumor necrosis factor", *Journal Immunol. Methods* 68:167–175.
13. Folstein et al. (1975) "Mini mental state: a practical method for grading cognitive state of patients for clinician", *J. Psych. Res.* 12:189–198.
14. Fudenberg and Singh (1988) "Alzheimer's 'syndrome': Prognosis of subsets with different etiology and preliminary effects of immunotherapy", *Drug Dev. Res.* 15:165–174.
15. Gautrin and Gauthier (1989) "Alzheimer's disease: environmental factors and etiologic hypotheses", *Can. J. Neurol. Sci.* 16:375–387.
16. Geokas et al. (1990) "The aging process", *Ann. Intern. Med.* 113:455–466.
17. Gillis et al. (1978) "T cell growth factor: parameters of production and quantitative microassay for activity", *J. Immunol.* 120:2027–2032.
18. Griffin et al. (1989) "Brain interleukin 1 and S-100 immunoreactivity are elevated in Down Syndrome/Alzheimer disease", *PNAS USA* 86:7611–7615.
19. Hachinski et al. (1974) "Multifarct dementia, a course of mental deterioration in the elderly", *Lancet* ii:207–208
20. Hulette and Walford (1987) "Immunological aspects of Alzheimer disease: a review", *Alzh. Dis. Assoc. Disord.* 1:72–82.
21. Ikeda et al. (1991) "Interleukin-2 receptor in peripheral blood lymphocytes of Alzheimer's disease patients", *Acta. Psychiatr. Scand.* 84:262–265.
22. Kalter and Kelly (1975) "Alzheimer's disease: evaluation of immunologic indices", *NY State J. Med.* 75:1222–1225.
23. Licastro et al. (1990) "Zinc and thymic hormone-dependent immunity in normal ageing . . . ", *J. Neuroimmunol.* 27:201–208.
24. Mayeux et al. (1985) "Heterogeneity in dementia of Alz. type: evidence of subgroups", *Neurology* 35:453–454.
25. McGeer et al. (1991) "Reactions of immune system in chronic degenerative neurological diseases", *Can. J. Neur. Sci.* 18:371–379.
26. McKann et al. (1984) "Clinical diagnosis of Alzheimer's disease" (Report of NINCDS-ADRDA Work Group) *Neurology* 34:939–949.
27. McRae and Dahlstrom (1992) "Immune responses in brains of Alzheimer and Parkinson's disease patients..", *Rev. Neuroscience* 3:79–97.
28. Merrill (1990) "Interleukin-2 effect in central nervous system", *NY Acad. Sci.* 594:188–199.
29. Miller et al. (1981) "Immunological studies in senile dementia of Alz. type: evid. for enhanced suppressor cell activity", *Ann. Neurol.* 10:506–510.
30. Miller (1989) "Minireview: The cell biology of aging: immun. models", *J. Gerontol.* 44:B4–B8.
31. Mills et al. (1985) "Increase in cytosolic free calcium concen. is an intracellular message for prod. of interleukin 2 . . . ", *J. Immunol* 134:1640–1649.
32. Namba et al. (1990) "Reactive microglias are positive for interleukin-2 and interleukin-6 in Alz. dementia brain", *J. Clin. Exp. Med.* 152:785–786.
33. Ortaldo et al. (1987) "Effects of natural and recombinant IL-2 on reg. of γIFN production and natural killer activity . . . ", *J. Immunol.* 133:779–783.
34. Rogers and Rovigatti (1988) "Immunologic and tissue culture approaches to neurobiology of aging", *Neurobiol. Aging* 9:759–762.
35. Roth (1986) "The Association of clinical and neurological findings and bearing on class and etiology of Alz. disease", *Br. Med. Bull.* 42:42–50.
36. Skias et al. (1985) "Senile dementia of Alz. type (SDAT): Red. T8+ cell-mediated supp. activity", *Neurology* 35:1635–1638.
37. Vandenabeele et al., (1991) "Is amyloidogenesis during Alzheimer's disease due to IL-1/IL-6 mediated 'acute phase response' in brain?" *Imm. Today* 12:217–219.
39. Weintraub et al. (1982) "Daily living activities in assess. of dementia", in *Alzheimer's disease: report of progress in research*, Raven Press, NY, pp. 109–192.
40. Zats and Goldstein (1985) "Thymosins, lymphokines and immunology of aging", *Gerontology* 31:263–277.

What is claimed is:

1. A method to assist in the diagnosis of possible Alzheimer's Disease in a patient comprising:

(a) assessing a numeric score for cognitive impairment in the patient according to a record of independent living (RIL) method:

(b) obtaining a blood sample from the assessment patient;

(c) measuring the lectin-stimulated production of IL-6, TNF-α, IFN-γ, and IL-2 cytokines and spontaneously secreted IL-3-LA from peripheral mononuclear cells from the blood sample; and (d) wherein a RIL score of 17–32, an increase in IL-6, decrease in IL-3-LA as compared to an age-matched healthy control or a RIL score, of 33–64, an increase in IL-6, TNF-α, IFN-γ, and IL-2 as compared to an age-matched healthy control, are indicative of a diagnosis of possible Alzheimer's Disease.

* * * * *